United States Patent [19]

Nonomura et al.

[11] Patent Number: 4,894,239

[45] Date of Patent: Jan. 16, 1990

[54] SUSTAINED-RELEASE PREPARATION AND PRODUCTION THEREOF

[75] Inventors: Muneo Nonomura; Yasuyuki Suzuki, both of Osaka; Masayuki Yamada, Hyogo, all of Japan

[73] Assignee: Takeda Chemical Industries, Ltd., Osaka, Japan

[21] Appl. No.: 194,210

[22] Filed: May 16, 1988

[30] Foreign Application Priority Data

Jun. 2, 1987 [JP] Japan .................................. 62-138781

[51] Int. Cl.⁴ ................................................ A61K 9/16
[52] U.S. Cl. ..................................... 424/497; 424/469; 424/489; 424/490; 424/494; 424/495; 424/496
[58] Field of Search ............... 424/486, 489, 488, 484, 424/79, 497, 463, 469

[56] References Cited

U.S. PATENT DOCUMENTS

| | | | |
|---|---|---|---|
| 2,990,332 | 6/1961 | Keating | 167/65 |
| 3,138,525 | 6/1964 | Koff | 167/65 |
| 3,313,686 | 4/1967 | Bryan et al. | 167/55 |
| 3,499,960 | 3/1970 | Macek et al. | 424/33 |
| 3,594,470 | 7/1971 | Borodkin et al. | 424/32 |
| 3,904,444 | 9/1975 | Anderson et al. | 424/486 X |
| 3,992,518 | 11/1976 | Chien et al. | 424/486 X |
| 4,221,778 | 9/1980 | Raghunathan | 424/31 |
| 4,548,990 | 10/1985 | Mueller et al. | 424/486 X |
| 4,668,506 | 5/1987 | Bawa | 424/486 X |
| 4,711,777 | 12/1987 | Tan et al. | 424/486 X |
| 4,741,872 | 5/1988 | De Luca et al. | 424/486 X |
| 4,794,002 | 12/1988 | Henis et al. | 424/486 X |

FOREIGN PATENT DOCUMENTS

| | | |
|---|---|---|
| 0154009 | 9/1985 | European Pat. Off. . |
| 0225615 | 6/1987 | European Pat. Off. . |
| 1908946 | 10/1969 | Fed. Rep. of Germany . |
| 2246037 | 4/1974 | Fed. Rep. of Germany . |
| 1218102 | 1/1971 | United Kingdom . |

Primary Examiner—Thurman K. Page
Attorney, Agent, or Firm—Wegner & Bretschneider

[57] ABSTRACT

The present invention concerns a sustained-release microcapsule preparation comprising an ion exchange resin with 6 to 16% crosslinking, containing a drug adsorbed in an amount not less than 80% of its theoretical ion adsorption amount and coated with a water-permeable polymer.

13 Claims, No Drawings

SUSTAINED-RELEASE PREPARATION AND PRODUCTION THEREOF

The present invention relates to a sustained-release preparation and the method of its production.

A variety of preparations which release the base drug so that the pharmacological effect of the drug lasts for a sustained period have been produced and tested. Such preparations included sustained-release preparations using an ion exchange resin. It has been reported that a drug-ion exchange resin complex is effective in releasing the drug in the digestive tract for a sustained period (e.g., see the specification for U.S. Pat. No. 2990332). However, when prepared as fine particles suitable for oral administration, e.g., particles of less than 500 μm diameter, the said drug-resin complex shows almost no sustained-release properties because its drug-releasing rate is too high.

Attempts have been made to prepare sustained-release microcapsules by coating the drug-resin complex with various materials to overcome this drawback and to thereby add a sustained-release property (e.g., see specifications for U.S. Pat. Nos. 3,138,525, 3,499,960, and 3,594,470).

When a sustained-release microcapsule obtained by coating a drug-resin complex with the material which has sustained-release properties on is orally administered, the drug is released by the exchange of ions in the digestive juice. The drug then passes through the sustained-release coat into the digestive juice where it is absorbed by the digestive tract. Then, the drug-resin complex absorbs water to swell. In the digestive tract, as a result, cracks are formed and rupture occurs in the sustained-release coat and the sustained-release property disappears. Also when a sustained-release microcapsule is formulated in an orally administered suspension, a similar problem arises in the preparation. These drawbacks have long been serious problems.

In relation to these drawbacks, it has also been reported that it is effective to pretreat the drug-resin complex with a solvating agent, such as polyethylene glycol, prior to the formation of the sustained-release coat on the complex (See specifications for U.S. Pat. No. 4,221,778).

Taking note of the excellent characteristic of the sustained-release preparation using a drug-resin complex, the present inventors worked to eliminate its drawbacks, and showed that the swelling of the drug-resin complex due to water absorption is closely related to the degree of crosslinking of the ion exchange resin and to the concentration of the drug thereby adsorbed. Thus the swelling of the drug-resin complex can be prevented by selecting the degree of the crosslinking of the resin and the drug concentration, and no rupture will occur even when the sustained-release coat is formed without pretreatment with a solvating agent.

In consideration of the fact that drugs are normally prepared in the form of salts for stabilization and other purposes, the present inventors made further investigations in order to establish a method of producing a drug-resin complex which does not swell and which maintains the drug at a high concentration from a salt of the corresponding drug using a process which is favorable for drug preparation. They thereby developed the present invention.

The present invention provides a sustained-release microcapsule preparation comprising an ion exchange resin with 6 to 16% of crosslinking, containing a drug adsorbed in an amount not less than 80% of its theoretical ion adsorption amount (the drug-resin complex), and coated with a water-permeable polymer coat, a method of producing the sustained-release microcapsule preparation comprising coating an ion exchange resin with 6 to 16% crosslinking and containing a drug adsorbed in an amount not less than 80% of its theoretical ion adsorption amount with a water-permeable polymer.

As for the ion exchange resin forming the abovementioned drug-resin complex, ordinary synthetic insoluble porous polymers, (e.g., the polymer which is the copolymer of styrene and divinylbenzene) may be mentioned.

Said polymer, when it is an acidic ion exchange resin (H type), contains sulfonic groups, carboxylic groups, etc., and adsorbs the basic drug; when it is a basic ion exchange resin (OH type), it contains primary to quaternary amino groups, etc., and adsorbs acidic drugs. In the present invention, in particular, it is preferable to use a strongly acidic or strongly alkaline ion exchange resin. The degree of crosslinking for the ion exchange resin is determined depending upon the amount of crosslinking agent such as divinylbenzene to be used; it is preferable that crosslinking is from 6 to 16%, especially from 8 to 14%.

These ion exchange resins are commercially available under the trade names of Diaion (Mitsubishi Chemical Industries Ltd., Japan), Dowex (Dow Chemical Co., USA), Amberlite (Röhm & Haas Co., USA), and others, and can be selected for use as appropriate.

It is preferable that the mean particle size of the ion exchange resin is from 5 to 1000 μm, specifically from 10 to 300 μm. If desired, a commercially available ion exchange resin may be crushed to fine particles before use by means of a mill such as an atomizer.

The theoretical ion adsorption amount (theoretical saturated adsorption amount, overall exchanging capacity) means the maximum amount of strongly basic ions (sodium ions, etc.) or strongly acidic ions (chlorine ions, etc.) adsorbed by a given ion exchange resin. For the present invention, an ion exchange resin which has adsorbed a drug in a molar ratio of more than 80%, specifically from 85 to 100% of this theoretical amount, is preferred.

Drugs having various effects can be selected depending upon the purpose, but it is preferable that the basic drug is of a pKa from 6 to 10, specifically a pKa from 7.5 to 10, and the acidic drug is of a pKa from 2 to 5. These drugs are normally present in the form of salts, basic drugs being available as salts with acids and acidic drugs being available as salts with bases.

As specific examples, the following may be mentioned:

Drugs for the respiratory tract:
Antitussive expectorants such as dihydrocodeine phosphate, codeine phosphate, noscapine hydrochloride, phenylpropanolamine hydrochloride, potassium guaiacolsulfonate, cloperastine fendizoate, dextromethorphan hydrobromide and chloperastine hydrochloride; bronchodilators such as dl-methylephedrine hydrochloride and dl-methylephedrine saccharinate; and antihistamines such as dl-chlorpheniramine maleate.

Drugs for the digestive tract:
Digestive tract antispasmodics such as scopolamine hydrobromide, metixene hydrochloride and dicyclomine hydrochloride.

Drugs for the central nervous system:

Antipsychotic drugs such as phenothiazine derivatives (chlorpromazine hydrochloride, etc.) and phenothiazine-like compounds (chlorprothixene hydrochloride, etc.); antianxiety drugs such as benzodiazepine derivatives (chlordiazepoxide hydrochloride, etc.); antidepressants such as imipramine compounds (imipramine hydrochloride, etc.); antipyretic analgesics such as sodium salicylate; and hypnotics such as phenobarbital sodium.

Drugs for the respiratory system:
Coronary dilators such as etafenone hydrochloride; antiarrhythmics such as procainamide hydrochloride; Ca antagonists such as verapamil hydrochloride; hypotensive drugs such as hydrazine hydrochloride, propranolol hydrochloride and clonidine hydrochloride; and peripheral vasodiaators/vasoconstrictors such as tolazoline hydrochloride.

Antibiotics:
Macrolides such as oleandomycin phosphate; tetracyclines such as tetracycline hydrochloride; streptomycins such as fradiomycin sulfate; and penicillin drugs such as dicloxacillin sodium, pivmecillinam hydrochloride and carbenicillinindanyl sodium.

Chemotherapeutic drugs:
Sulfa drugs such as sulfisomidine sodium; antituberculosis drugs such as kanamycin sulfate; and antiprotozoan drugs such as amodiaquine hydrochloride.

In particular, an excellent sustained releasing effect is obtained in basic drugs for the respiratory tract such as dihydrocodeine phosphate, dl-methyl-ephedrine hydrochloride and phenylpropanolamine hydrochloride.

The water-permeable polymer coat is formed of a natural or non-natural biocompatible polymer. Examples of such polymers, include cellulose polymers such as ethylcellulose, nitrocellulose, benzylcellulose, acetocellulose, hydroxypropylcellulose and cellulose acetate propionate; and non-natural polymers such as polyacrylate, polymethacrylate, polyamide and acrylatemethacrylate copolymers (e.g., aminoalkyl methacrylate copolymer). For the present invention, in particular, aminoalkyl methacrylates (known as Eudragit, etc.) are favored The sustained-release preparation of this invention can be, for example, produced as follows:

In an aqueous solvent capable of dissolving both salts and the free form of the drug, a drug in a salt form is reacted with an ion exchange resin to give an aqueous solution of the free form of the drug.

Examples of aqueous solvents include organic solvents which are freely soluble in water such as primary, lower ($C_{1-3}$) alcohols (e.g., methanol, ethanol, isopropanol) and aqueous solutions of ketones such as acetone and methyl ethyl ketone.

Said aqueous solvents mentioned include aqueous solutions containing from 5 to 95%, preferably from 10 to 90%, of the organic solvent. In particular, when the salt is of a basic drug, it is preferable to use an aqueous solution of from 40 to 85% ethanol or isopropanol, and when the salt is of an acidic drug, to use an aqueous solution of from 5 to 30% ethanol.

The ion exchange resin to be used in the reaction may be those mentioned above, i.e. a basic ion exchange resin is used for a basic drug and an acidic ion exchange is used for an acidic drug to make respective free forms.

The reaction with the ion exchange resin is carried out by adding an ion exchange resin as mentioned above to the salt of the drug in solution in the aqueous solvent and then stirring the mixture. In this case, it is preferable that the ion exchange resin is used in an amount from 1.0 to 2.0 times the necessary amount of the drug's salt. The reaction is normally carried out at room temperature or ambient temperature, but the mixture can be warmed to about 70° C. Reaction time is from 0.5 to 6 hours.

After the completion of reaction, the ion exchange resin is removed by ordinary means, then an aqueous solution of the free form of the drug is provided.

The drug-resin complex can be produced by adding an ion exchange resin of a given particle size and degree of crosslinking to the above aqueous solution and causing a reaction between them. The reaction is normally carried out at room temperature with from 0.5 to 3 hours of stirring.

The above reaction will give a drug-ion exchange resin complex which has adsorbed the drug in an amount of more than 80% of the theoretical ion adsorption amount, and it is preferable that the complex used contain the adsorbed drug in an amount of from 85 to 100% of the theoretical ion adsorption amount.

Said complex is then coated with a water-permeable polymer to produce the microcapsule preparation of this invention. For coating with the water-permeable polymer, organic solvents capable of dissolving polymers are used, such as ethanol, toluene, chloroform, methyl ethyl ketone, methylene chloride, isopropanol, cyclohexane, methanol, ethylene chloride, dimethylformamide, or ethyl acetate A plasticizer or a stabilizer, such as an antioxidant, may also be added in any amount. Examples of plasticizers include dibasic acid esters (phthalic acid esters, etc.), glycol esters, and fatty acid esters. Examples of antioxidants for stabilization include 2(3)-t-butyl-4-hydroxyanisol(BHA), 3,5-di-t-butyl-4-hydroxytoluene(BHT), tocopherol and tocopherol acetate.

When the water-permeable polymer is an acrylatemethacrylate copolymer, it is dissolved in methylene chloride or chloroform, the drug-resin complex then is added to and suspended in this solution. The resulting suspension is treated mechanically by the spray drying method to produce microcapsules; this can also be done by phase separation, a physico-chemical method. In this procedure the polymer is dissolved in a good solvent, a phase separating and anti-aggregating agent (chosen from polybutadiene, polydimethylsiloxane, methacryl polymer, etc.) is added to it in any amount, and a nonsolvent is added while the solution is being stirred. Microcapsules can also be produced by a chemical method, i.e., the interfacial polymerization method. No matter which method is employed, it is preferable that the particle size of the sustained-release microcapsules thus obtained be from 5 to 1000 μm, or, more preferably, from 10 to 300 μm.

For producing an oral suspension of the sustained-release microcapsules, purified water (as specified by the Pharmacopoea of Japan) can be used as the solvent. Usually, the total amount of about 0.2 g to 10 g of the microcapsule is suspended in 100 ml of purified water. Antiseptics, correctives, dispersing agents, wetting agents, thickening agents, etc., may be added as required.

As antiseptics, non-ionic methyl parahydroxybenzoate, ethyl parahydroxybenzoate, propyl parahydroxybenzoate, butyl parahydroxybenzoate, etc., may be used. As correctives, sucrose, fructose, lactose, sorbitol, mannitol, etc., may be used. As wetting agents, surfactants such as polyoxyethylene sorbitan fatty acid esters (Polysorbate 80, Arlacel 83, etc.), polyoxyethylene hardened castor oils (HCO-50, etc.) and sugar esters may be added. As dispersing agents or thickening agents, guaiac gum, pullulan, xanthan gum, carrageenan, tragacanth gum, dextrin, pectin, gelatin, locust bean gum, guar gum etc., may be added in any amount. In addition to these additives, non-ionic substances may also be added as required.

The microcapsule preparation of this invention may be prepared as capsules in which the microcapsules are filled as well as a sustained-release suspension directly to be taken orally. The microcapsules may also be suspended in an oily substance such as olive oil or safflower oil to provide soft gelatin-like capsules. The microcapsule preparation may also be combined with lactose, sucrose, corn starch, hydroxypropylcellulose, etc., to provide granules, powders or tablets The sustained-release preparation of this invention is characterized as follows:

(1) A drug-ion exchange resin complex is produced in a continuous process in which a salt of a basic drug ( or a salt of an acidic drug) is reacted in an aqueous solvent with a basic ion exchange resin ( or an acidic ion exchange resin) to give the free form of the drug, which can then be adsorbed by desired ion exchange resin. In this way, a complex is obtained which has adsorbed the drug in an amount nearer to the theoretical saturated adsorption amount than by the conventional production process based on equilibrium reaction; repetitive adsorption processes are not necessary, and drug loss is very small. In addition, it is possible to minimize the dose of the microcapsules making them economical, as well as easy to take; this dosage form design facilitates drug development.

(2) In the present invention, the drug-resin complex can be produced with high efficiency because a higher drug adsorption rate is achieved as a result of the swelling of the ion exchange resin in the aqueous solvent, specifically a mixture of water and ethanol or methanol, to a higher degree than in the case in which water alone is used.

(3) Since the drug-resin complex which has adsorbed the drug in a high concentration is coated with a water-permeable polymer which has a sustained-release property, the coats of microcapsules show neither cracking nor breaking (rupture) even when they are dispersed or suspended in a solvent. The greater the molecular weight of the drug, or the sterically bulkier the structure of the drug, the less likely the rupture is to occur. Dosage form designing can be done efficiently without using additives such as plasticizers in the coating materials as was previously done, thus ensuring the production of a preparation exhibiting an effective sustained-release property.

EXAMPLE

The present invention will now be illustrated in more detail by means of the following working and comparative examples.

EXAMPLE 1

14 g of methylephedrine hydrochloride was dissolved in 50 ml of a 60% methanol solution. To the resulting solution, 70 g of an anion exchange resin [OH type; Diaion SAN1 (Mitsubishi Chemical Industries)] was added followed by 1 hour of agitation. The slurry was then separated by filtration, and the ion exchange resin separated by filtration was washed with 300 ml of a 60% methanol solution. The washings were combined with the former filtrate, and diluted with a 60% methanol solution to 500 ml.

Determinations of the total content of the methylephedrine hydrochloride and the free base in this 500 ml solution were made by high performance liquid chromatography. And the content of the free base was determined by titration. Methylephedrine as a hydrochloride was not detected, i.e., 100% of the methylephedrine hydrochloride was converted to the free base. The content was calculated as 13.8 g methylephedrine hydrochloride, the recovery was 98.6%.

Then, to a 450 ml portion of this solution was added 24.3 g (the amount in which the degree of methylephedrine adsorption will be 90% of the theoretical saturated adsorption amount for the ion exchange resin) of a cation exchange resin containing 8% divinylbenzene (degree of crosslinking: 8%) [H type; Diaion SKNUPC (Mitsubishi Chemical Industries)], and the reaction was carried out for 1 hour while stirring the solution. After completion of the reaction, the filtrate was assayed for methylephedrine but no methylephedrine was detected. This meant that the entire amount of methylephedrine in the form of the free base in the solution was bound to the ion exchange resin.

The methylephedrine resinate separated by filtration was dried, and this 2.8 g portion was dispersed in a solution of 1 g aminoalkyl methacrylate copolymer RS [Eudragit RS100 (Röhm Pharma)] in 5 ml methylene chloride. The resulting slurry was subjected to spray drying to give microcapsules. The methylephedrine sustained-release property of the microcapsules thus obtained was evaluated by means of a dissolution test (JP XI Paddle Method, using 500 ml of a 0.2 M NaCl solution which contains 0.05% Tween 80, as the eluant). The results are shown in Table 1. A good sustained-release property was exhibited, and no occurrence of rupture (such as cracking or breaking) in the microcapsule coat was noted in the scanning electron microscopy following the dissolution test.

TABLE 1

| Time (hours) elapsed after initiation of the dissolution test | Rate (%) of methylephedrine dissolution from the microcapsules |
| --- | --- |
| 0 | 0 |
| 0.5 | 18.4 |
| 1.0 | 26.1 |
| 2.0 | 39.9 |
| 3.0 | 48.7 |
| 4.5 | 57.1 |
| 6.0 | 67.5 |
| 8.0 | 74.8 |

EXAMPLE 2

12 g of methylephedrine hydrochloride was dissolved in 150 ml of a 50% isopropyl alcohol solution. To the resulting solution, 70 g of the same anion exchange resin (OH type) as in Example 1 was added, and this was followed by 1 hour of agitation. Then, the slurry was separated by filtration, and the ion exchange resin separated by filtration was washed with 300 ml of a 50% isopropyl alcohol solution. The washings were combined with the former filtrate, and diluted with a 50% isopropyl alcohol solution to 500 ml.

Determinations of the total content of the methylephedrine hydrochloride and the free base in this 500 ml solution were made by high performance liquid chromatography and the content of the free base was determined by titration method; methylephedrine as a hydrochloride was not detected, i.e., 100% of the methylephedrine hydrochloride was converted to the free base. The content was calculated as 11.2 g methylephedrine hydrochloride, the recovery was 93.3%.

Then, to a 450 ml portion of this solution was added 22.1 g (the amount in which the degree of methylephedrine adsorption will be 85% of the theoretical saturated adsorption amount for the ion exchange resin) of a cation exchange resin containing 10% divinylbenzene (degree of crosslinking: 10%) [H type; Diaion SK110 (Mitsubishi Chemical Industries)], and the reaction was carried out for 1 hour while stirring the solution. After the completion of the reaction, the filtrate was assayed for methylephedrine, but no methylephedrine was detected. This meant that the entire amount of methylephedrine in the form of the free base in the solution was bound to the ion exchange resin.

The methylephedrine resinate separated by filtration was dried, and this 3.1 g portion was dispersed in a solution of 0.7 g aminoalkyl methacrylate copolymer RS [Eudragit RS100 (Röhm Pharma)] and 0.3 g aminoalkyl methacrylate copolymer RL [Eudragit RS100L (Röhm Pharma)] in 4 ml chloroform. Then, 10 ml cyclohexane was slowly added to this slurry to induce coacervation to such a degree that no coagulation would occur. This slurry was then subjected to spray drying to give microcapsules. The methylephedrine sustained-release property of the microcapsules thus obtained was evaluated by means of a dissolution test (JP XI Paddle Method, using 500 ml of a 0.2M NaCl solution which contains 0.05% Tween 80, as the eluant). The results are shown in Table 2. A good sustained-release property was exhibited, and no occurrence of rupture (such as cracking or breaking) in the microcapsule coat was noted in the scanning electron microscopy following the dissolution test.

TABLE 2

| Time (hours) elapsed after initiation of the dissolution test | Rate (%) of methylephedrine dissolution from the microcapsules |
| --- | --- |
| 0 | 0 |
| 0.5 | 10.5 |
| 1.0 | 30.8 |
| 2.0 | 49.5 |
| 3.0 | 64.8 |
| 4.5 | 77.7 |
| 6.0 | 87.4 |
| 8.0 | 96.5 |

EXAMPLE 3

10 g of dihydrocodeine phosphate was dissolved in 250 ml of a 50% ethanol solution. To the resulting solution, 30 g of the same anion exchange resin (OH type) as in Example 1 was added, and this was followed by 2 hours of agitation. Then, the slurry was separated by filtration, and the ion exchange resin separated by filtration was washed with 300 ml of a 50% ethanol solution. The washings were combined with the former filtrate, and diluted with a 50% ethanol solution to 500 ml.

Determinations of the total content of the dihydrocodeine phosphate and the free base in this 500 ml solution were made by high performance liquid chromatography and the content of the free base was determined by titration method; dihydrocodeine as a phosphate was not detected, i.e., 100% of the dihydrocodeine phosphate was converted to the free base. The content was calculated as 9.8 g dihydrocodeine phosphate, the recovery was 98.0%.

Then, to a 450 ml portion of this solution was added 25.69 g (the amount in which the degree of dihydrocodeine adsorption will be 85% of the theoretical saturated adsorption amount for the ion exchange resin) of a cation exchange resin containing 8% divinylbenzene (degree of crosslinking: 8%) [H type; Diaion SKNUPC (Mitsubishi Chemical Industries)], and the reaction was carried out for 1 hour while stirring the solution. After the completion of the reaction, the filtrate was assayed for dihydrocodeine, but no dihydrocodeine was detected. This meant that the entire amount of the dihydrocodeine in the form of the free base in the solution was bound to the ion exchange resin.

The dihydrocodeine resinate separated by filtration was dried, and a 3.3 g portion was dispersed in a solution of 0.8 g aminoalkyl methacrylate copolymer RS [Eudragit RS100 (Röhm Pharma)] and 0.2 g aminoalkyl methacrytate copolymer RL [Eudragit RS100L (Röhm Pharma)] in 8 ml acetone. This slurry was subjected to spray drying to give microcapsules. The dihydrocodeine sustained-release property of the microcapsules thus obtained was evaluated by means of a dissolution test (JP XI Paddle Method, using 500 ml of a 0.2 M NaCl solution which contains 0.05% Tween 80, as the eluant). The results are shown in Table 3. A good sustained-release property was exhibited, and no occurrence of rupture (such as cracking or breaking) in the microcapsule coat was noted in the scanning electron microscopy following the dissolution test.

TABLE 3

| Time (hours) elapsed after initiation of the dissolution test | Rate (%) of dihydrocodeine dissolution from the microcapsules |
| --- | --- |
| 0 | 0 |
| 0.5 | 10.7 |
| 1.0 | 24.8 |
| 2.0 | 46.8 |
| 3.0 | 59.1 |
| 4.5 | 74.5 |
| 6.0 | 80.2 |
| 8.0 | 88.3 |

EXAMPLE 4

10 g of dihydrocodeine phosphate was dissolved in 250 ml of a 50% ethanol solution. To the resulting solution, 30 g of the same anion exchange resin (OH type) as in Example 1 was added, and this was followed by 2 hours of agitation. Then, the slurry was separated by filtration, and the ion exchange resin separated by filtration was washed with 300 ml of a 50% ethanol solution. The washings were combined with the former filtrate, and diluted with a 50% ethanol solution to 500 ml.

Determinations of the total content of the phosphate and the free base in this 500 ml solution were made by high performance liquid chromatography, and the content of the free base was determined by titration method; dihydrocodeine as a phosphate was not detected, i.e., 100% of the dihydrocodeine phosphate was converted to the free base. The content was calculated as 9.8 g dihydrocodeine phosphate, the recovery being 98.0%.

Then, to a 450 ml portion of this solution was added 26.0 g (the amount in which the degree of dihydrocodeine adsorption will be 90% of the theoretical saturated adsorption amount for the ion exchange resin) of a cation exchange resin containing 6% divinylbenzene (degree of crosslinking: 6%) [H type; Diaion SK106 (Mitsubishi Chemical Industries)], and the reaction was carried out for 1 hour while stirring the solution. After the completion of the reaction, the filtrate was assayed for dihydrocodeine, but no dihydrocodeine was detected. This meant that the entire amount of dihydrocodeine in the form of the free base in the solution was bound to the ion exchange resin.

The dihydrocodeine resinate separated by filtration was dried, and this 3.3 g portion was dispersed in a solution of 1.0 g aminoalkyl methacrylate copolymer RS [Eudragit RS100 (Röhm Pharma)] and 0.5 g polyisobutylene (MW: 400,000) in 5 ml chloroform. Then, to this slurry, a solution of 2.5 g polyisobutylene in 40 ml cyclohexane was added by drops while stirring the slurry. After this solution was added, microcapsules were separated by filtration. The polyisobutylene was washed away with cyclohexane, and the microcapsules were dried. The dihydrocodeine sustained-release property of the microcapsules was evaluated by means of a dissolution test (JP XI Paddle Method, using 500 ml of a 0.2M NaCl solution which contains 0.05% Tween 80, as the eluant). The results are shown in Table 4. A good sustained-release property was exhibited, and no occurrence of rupture (such as cracking or breaking) in the microcapsule coat was noted in the scanning electron microscopy following the dissolution test.

TABLE 4

| Time (hours) elapsed after initiation of the dissolution test | Rate (%) of dihydrocodeine dissolution from the microcapsules |
| --- | --- |
| 0 | 0 |
| 0.5 | 5.3 |
| 1.0 | 10.2 |
| 2.0 | 16.8 |
| 3.0 | 32.5 |
| 4.5 | 40.1 |
| 6.0 | 52.0 |
| 8.0 | 65.1 |

EXAMPLE 5

31 g of dextromethorphan hydrobromide was dissolved in 600 ml of a 85% ethanol solution. To the resulting solution, 75 g of the same anion exchange resin (OH type) as in Example 1 was added, and this was followed by 2 hours of agitation. The slurry was then separated by filtration, and the ion exchange resin separated by filtration was washed with 200 ml of a 85 % ethanol solution. The washings were combined with the former filtrate, and diluted with a 85% ethanol solution to 1000 ml.

Determinations of the total content of the dextramethorphan hydrobromide and the free base was made by high performance liquid chromatography, and the content of free base was determined by titration; dextromethorphan as hydrobromide was not detected, i.e., 100% of the dextromethorphan hydrobromide was converted to the free base. The content was calculated as 30.2 g dextromethorphan hydrobromide, the recovery was 97.4%.

Then, to a 440 ml portion of this solution was added 16.25 g (the amount in which the degree of dextromethorphan adsorption will be 82% of the theoretical saturated adsorption amount for the ion exchange resin) of a cation exchange resin containing 8% divinylbenzene (degree of crosslinking: 8%) [H type; Diaion SKNUPC (Mitsubishi Chemical Industries)], and the reaction was carried out for 1 hour while stirring the solution. After the completion of the reaction, the filtrate was assayed for dextromethorphan, but no dextromethorphan was detected. This meant that the entire amount of dextromethorphan in the form of the free base in the solution was bound to the ion exchange resin.

The dextromethorphan resinate separated by filtration was dried, and this 3.3 g portion was dispersed in a solution of 1.0 g ethylcellulose 100 cp in 20 ml of methylene chloride. This slurry was then subjected to spray drying. The dextromethorphan sustained-release property of the microcapsules thus obtained was evaluated by means of a dissolution test (JP XI Paddle Method, using 500 ml of a 0.2M NaCl solution which contains 0.05% Tween 80, as the eluant). The results are shown in Table 5. A good sustained-release property was exhibited, and no occurrence of rupture (such as cracking or breaking) in the microcapsule coat was noted in the scanning electron microscopy following the dissolution test.

TABLE 5

| Time (hours) elapsed after initiation of the dissolution test | Rate (%) of dextromethorphan dissolution from the microcapsules |
| --- | --- |
| 0 | 0 |
| 0.5 | 38.3 |
| 1.0 | 56.2 |
| 2.0 | 79.1 |
| 3.0 | 88.7 |
| 4.5 | 95.0 |
| 6.0 | 100.0 |

EXAMPLE 6

20 g of chlorpheniramine maleate was dissolved in 1000 ml of a 55% ethanol solution. To the resulting solution, 35 g of the same anion exchange resin (OH type) as in Example 1 was added, and this was followed by 2 hours of agitation. Then, the slurry was separated by filtration, and the ion exchange resin separated by filtration was washed with 300 ml of a 55% ethanol solution. The washings were combined with the former filtrate, and diluted with a 55% ethanol solution to 1500 ml.

Determinations of the total content of the chlorpheniramine maleate and the free base in this 1500 ml solution were made by high performance liquid chromatography, and the content of the free base was determined by titration; chlorpheniramine as the maleate was not detected, i.e., 100% of the chlorpheniramine maleate was converted to the free base. The content was calculated as 19.5 g chlorpheniramine maleate, the recovery being 97.5%.

Then, to a 1000 ml portion of this solution was added 17.98 g (the amount in which the degree of chlorpheniramine adsorption will be 80% of the theoretical saturated adsorption amount for the ion exchange resin) of a cation exchange resin containing 6% divinylbenzene (degree of crosslinking: 6%) [H type; Diaion SK106 (Mitsubishi Chemical Industries)], and the reaction was carried out for 1 hour while stirring the solution. After the completion of the reaction, the filtrate was assayed for chlorpheniramine, but no chlorpheniramine was detected. This meant that the entire amount of chlorpheniramine in the form of free base in the solution was bound to the ion exchange resin.

The chlorpheniramine resinate separated by filtration was dried, and this 2.8 g portion was dispersed in a solution of 0.7 g aminoalkyl methacrylate copolymer RS [Eudragit RS100 (Röhm Pharma)], 0.2 g aminoalkyl methacrylate copolymer RL [Eudragit RS100L (Röhm Pharma)], and 0.05 g medium-chain fatty acid triglyceride in 6 ml methyl ethyl ketone. This slurry was then subjected to spray drying. The chlorpheniramine sustained-release property of the microcapsules thus obtained was evaluated by means of a dissolution test (JP XI Paddle Method, using 500 ml of a 0.2 M NaCl solution which contains 0.05% Tween 80, as the eluant). The results are shown in Table 6. A good sustained-release property was exhibited, and no occurrence of rupture (such as cracking or breaking) in the microcapsule coat was noted in the scanning electron microscopy following the dissolution test.

TABLE 6

| Time (hours) elapsed after initiation of the dissolution test | Rate (%) of chlorpheniramine dissolution from the microcapsules |
| --- | --- |
| 0 | 0 |
| 0.5 | 19.3 |
| 1.0 | 38.5 |
| 2.0 | 57.9 |
| 3.0 | 72.2 |
| 4.5 | 84.0 |
| 6.0 | 88.5 |
| 8.0 | 92.4 |

EXAMPLE 7

35 g of phenylpropanolamine hydrochloride was dissolved in 400 ml of a 50% ethanol solution. To the resulting solution, 200 g of the same anion exchange resin (OH type) as in Example 1 was added, and this was followed by 2 hours of agitation. The slurry was then separated by filtration, and the ion exchange resin thus separated was washed with 100 ml of a 50% ethanol solution. The washings were combined with the former filtrate, and diluted with a 50% ethanol solution to 500 ml.

Determinations of the total content of the phenylpropanolamine hydrochloride and the free base in this 500 ml solution were made by high performance liquid chromatography, and the content of the free base was determined by titration method phenylpropanolamine as a hydrochloride was not detected, i.e., 100% of the phenyl-propanolamine hydrochloride was converted to the free base. The content was calculated as 34.8 g phenylpropanolamine hydrochloride, the recovery was 99.5%.

Then, to a 300 ml portion of this solution was added 38 1 g (the amount in which the degree of phenylpropanolamine adsorption will be 100% of the theoretical saturated adsorption amount for the ion exchange resin) of a cation exchange resin containing 8% divinylbenzene (degree of crosslinking: 8%) [H type; Diaion SKNUPC (Mitsubishi Chemical Industries)], and the reaction was carried out for 1 hour while stirring the solution. After completion of the reaction, the filtrate was assayed for phenylpropanolamine, but no phenylpropanolamine was detected. This meant that the entire amount of phenylpropanolamine in the form of the free base in the solution was bound to the ion exchange resin.

The phenylpropanolamine resinate separated by filtration was dried, and this 3.0 g portion was dispersed in a solution of 0.7 g aminoalkyl methacrylate copolymer RS Eudragit RS100 (Röhm Pharma)] in 6 ml methylene chloride. This slurry was then subjected to spray drying. The phenylpropanolamine sustained-release property of the microcapsules thus obtained was evaluated by means of a dissolution test (JP XI Paddle Method, using 500 ml of a 0.2M NaCl solution which contains 0.05% Tween 80, as the eluant). The results are shown in Table 7. A good sustained-release property was exhibited, and no occurrence of rupture (such as cracking or breaking) in the microcapsule coat was noted in the scanning electron microscopy following the dissolution test.

TABLE 7

| Time (hours) elapsed after initiation of the dissolution test | Rate (%) of phenylpropanolamine dissolution from the microcapsules |
| --- | --- |
| 0 | 0 |
| 0.5 | 33.7 |
| 1.0 | 45.6 |
| 2.0 | 61.5 |
| 3.0 | 71.0 |
| 4.5 | 76.5 |
| 6.0 | 80.6 |
| 8.0 | 84.2 |

EXAMPLE 8

3.3 g the dihydrocodeine resinate prepared in Example 3 (the degree of dihydrocodeine adsorption onto the cation exchanger resin containing 8% divinylbenzene (degree of crosslinking: 8%) [H type; Diaion SKNUPC Mitsubishi Chem. Ind.)] was 85% of the theoretical saturated adsorption amount for the ion exchange resin) was dispersed into a solution of 0.8 g aminoalkyl methacrylate copolymer RS [Eudragit RS100 (Röhm Pharma)] and 0.2 g aminoalkyl methacrylate copolymer RL [Eudragit RS100L (Röhm Pharma)] in 5 ml of methylene chloride. To this resulting slurry, 2 ml of 50% ethanol solution was added, and this slurry was well-agitated. This final slurry was subjected to spray drying to produce microcapsules.

On the other hand, the methylephedrine resinate was prepared from the methylephedrine free base solution as in Example 1 and the cation exchanger resin containing 12% divinylbenzene (degree of crosslinking: 12%) [H type: Diaion SK-112 (Mitsubishi chemical Industries)]. This resinate was 82% of the theoretical saturated adsorption amount for the ion exchanger resin. 3 g of this methylephedtine resinate was dispersed into a solution of 10 g aminoalkyl methacrylate copolymet RS [Eudragit RS100 (Röhm Pharma)] in 5 ml of methylene chloride. To this resulting slurry, 2 ml of 50% ethanol solution was added, and this slurry was well-agitated. This final slurry was subjected to spray drying to produce microcapsules.

EXAMPLE 9

Two above sustained-release microcapsules in Example 8, the dihydrocodeine-microcapsule and the methylephedrine microcapsule, and clorpheniramine microcapsule in Example 6 were used to produce the syrup of a sustained-release suspension to be taken orally as an antitussive expectorant preparation, the formula I of which was the following.

| formula I | |
|---|---|
| dihydrocodeine SR-microcapsule | 12.5 g |
| methylephedrine SR-microcapsule | 45.0 g |
| chlorphenyramine SR-microcapsule | 4.9 g |
| guaiacol glyceryl ether | 8.0 g |
| caffein anhydrate | 10.0 g |
| D-sonbitol | 1.0 kg |
| sucrose | 1.0 kg |
| locust bean gum | 10.0 g |
| benzoic acid | 3.0 g |
| butyl p-hydroxybenzoate | 0.25 g |
| Tween 80 | 0.5 g |
| Total (added purified water) | 5.0 l |

The procedure for making above syrup is detailed below.

2.0 l of purified water was heated to about 85° C. and 3 g of benzoic acid and 0.25 g butyl p-hydroxybenzoate were dissolved therein. Then after cooling, 0.5 g Tween 80 was added following addition of 10 g locust bean gum. Then, 10 g of caffeins anhydrate and 8 g of guaiacol glycerylether were dissolved, and 1 kg of D-sorbitol and 1 kg of sucrose were added and dissolved. Three kinds of SR-microcapsule were wetted and suspended into 1 l purified water containing 0.5 g Tween 80. Above syrup and suspension containing these three kinds of SR-microcapsule were mixed, then the total volume became 5 l by addition of purified water.

The obtained suspension is administered to an adult in an amount of 10 ml each per day.

COMPARATIVE EXAMPLE 1

5 g of potassium guaiacolsulfonate was dissolved in 500 ml of distilled water. To the resulting solution, 6.08 g of an anion exchange resin containing 8% divinylbenzene (degree of crosslinking: 8%) [OH type; Diaion SAN1 (Mitsubishi Chemical Industries)] was added, and this was followed by 3 hours of agitation (the mixing ratio was such that the amount of potassium guaiacolsulfonate was 200% of the equivalent of the ion exchange resin). The resulting slurry was then filtrated, and the filtrate was assayed for potassium guaiacolsulfonate; it was found that 36.3% of the initial amount was bound to the resin and 63.7% of the initial amount remained in the filtrate.

In the produced guaiacolsulfonic acid resinate, 71.3% of the ion exchange resin's exchange groups had guaiacolsulfonic acid bound thereto.

The produced resinate was then separated by filtration and dried. This 2.5 g portion was dispersed in a solution of 1.0 g aminoalkyl methacrylate RS [Eudragit RS100 (Röhm Pharma)] in 5.0 ml methylene chloride. The slurry thus obtained was sprayed for coating; the resulting microcapsules were dried. Guaiacolsulfonic acid dissolution from the microcapsules was tested at 37° C. using the dissolution test apparatus of the JP XI. As the eluant, 500 ml of a 0.2M NaCl solution which contains 0.05% Tween 80 was used. The results are shown in Table 8. Bursting due to rupture was noted immediately after initiation of the test, and also the sustained-release property was not good. In scanning electron microscopy following the test, the occurrence of ruptures such as cracking and breaking was noted in the microcapsule coat due to the swelling of the resinate.

TABLE 8

| Time (hours) elapsed after initiation of the dissolution test | Rate (%) of guaiacolsulfonic acid dissolution from the microcapsules |
|---|---|
| 0 | 0 |
| 0.25 | 60.5 |
| 0.5 | 82.5 |
| 1.0 | 92.2 |
| 2.0 | 95.3 |
| 3.0 | 97.0 |
| 5.0 | 98.0 |

COMPARATIVE EXAMPLE 2

5 g of potassium guaiacolsulfonate was dissolved in 500 ml of distilled water. To the resulting solution was added 23.9 g of an anion exchange resin containing 8% divinylbenzene (degree of crosslinking: 8%) [OH type; Diaion SAN1 (Mitsubishi Chemical Industries)], and this was followed by 3 hours of agitation (the mixing ratio was such that the amount of potassium guaiacolsulfonate was 50.8% of the equivalent of the ion exchange resin). The resulting slurry was then filtered, and the filtrate was assayed for potassium guaiacolsulfonate; it was found that 92.1% of the initial amount was bound to the resin, 7.9% of the initial amount remained in the filtrate.

In the produced guaiacolsulfonic acid resinate, 46.8% of the ion exchange resin's exchange groups had guaiacolsulfonic acid bound thereto.

The produced resinate was then separated by filtration and dried. This 2.0 g portion was dispersed in a solution of 1.0 g of aminoalkyl methacrylate RS [Eudragit RS100 (Röhm Pharma)] in 5.0 ml methylene chloride. The slurry thus obtained was sprayed for coating; the resulting microcapsules were dried. Guaiacolsulfonic acid dissolution from the microcapsules was tested at 37° C. using the dissolution test apparatus of the JP XI. As the eluant, 500 ml of a 0.2M NaCl solution which contains 0.05% Tween 80 was used. The results are shown in Table 9. Bursting due to rupture was noted immediately after initiation of the test, and also the sustained-release property was not good. In scanning electron microscopy following the test, the occurrence of ruptures such as cracking and breaking was noted in the microcapsule coat due to the swelling of the resinate.

TABLE 9

| Time (hours) elapsed after initiation of the dissolution test | Rate (%) of guaiacolsulfonic acid dissolution from the microcapsules |
|---|---|
| 0 | 0 |
| 0.25 | 92.5 |
| 0.5 | 95.5 |
| 1.0 | 96.0 |
| 2.0 | 97.3 |
| 3.0 | 98.0 |
| 5.0 | 99.3 |

COMPARATIVE EXAMPLE 3

10 g of phenylpropanolamine hydrochloride was dissolved in 500 ml of distilled water. To the resulting solution was added 25.81 g of a cation exchange resin containing 8% divinylbenzene (degree of crosslinking:

8%) [H type; Diaion SKNUPC (Mitsubishi Chemical Industries)], and this was followed by 3 hours of agitation (the mixing ration was such that the amount of phenylpropanolamine hydrochloride was 74.2% of the equivalent of the ion exchange resin). The resulting slurry was filtered, and the filtrate was assayed for phenylpropanolamine hydrochloride; it was found that 84.0% of the initial amount was bound to the resin, 16.0% of the initial amount remained in the filtrate.

In the produced phenylpropanolamine resinate, 62.3% of the ion exchange resin's exchange groups had phenylpropanolamine bound thereto.

The produced resinate was then separated by filtration and dried. This 2.8 g portion was dispersed in a solution of 1.0 g aminoalkyl methacrylate RS [Eudragit RS100 (Röhm Pharma)] in 5.0 ml of methylene chloride. The slurry thus obtained was sprayed for coating; the resulting microcapsules were dried. Phenylpropanolamine dissolution from the microcapsules was tested at 37° C. using the dissolution test apparatus of the JP XI. As the eluant, 500 ml of a 0.2 M NaCl solution which contains 0.05% Tween 80 was used. The results are shown in Table 10. Bursting due to rupture was noted immediately after initiation of the test, and also the sustained-release property was not good. In scanning electron microscopy following the test, the occurrence of ruptures such as cracking and breaking 0 was noted in the microcapsule coat due to the swelling of the resinate.

TABLE 10

| Time (hours) elapsed after initiation of the dissolution test | Rate (%) of phenylpropanolamine dissolution from the microcapsules |
|---|---|
| 0 | 0 |
| 0.25 | 46.8 |
| 0.5 | 61.2 |
| 1.0 | 79.5 |
| 2.0 | 90.1 |
| 3.0 | 95.0 |
| 5.0 | 98.3 |

COMPARATIVE EXAMPLE 4

10 g of methylephedrine hydrochloride was dissolved in 500 ml of distilled water. To the resulting solution was added 34.6 g of a cation exchange resin containing 8% divinylbenzene (degree of crosslinking: 8%) [H type; Diaion SKNUPC (Mitsubishi Chemical Industries)], and this was followed by 3 hours of agitation (the mixing ratio was such that the amount of methylephedrine hydrochloride was 48.4% of the equivalent of the ion exchange resin); it was found that 93.0% of the initial amount was bound to the resin, 7.0% of the initial amount remaining in the filtrate.

In the produced methylephedrine resinate, 45.0% of the ion exchange resin's exchange groups had methylephedrine bound thereto.

The produced resinate was then separated by filtration and dried. This 2.2 g portion was dispersed in a solution of 1.0 g aminoalkylmethacrylate RS [Eudragit RS100 (Röhm Pharma)] in 5.0 ml of methylene chloride. The slurry thus obtained was sprayed for coating; the resulting microcapsules were dried. Methylephedrine dissolution from the microcapsules was tested at 37° C. using the dissolution test apparatus of the JP XI. As the eluant, 500 ml of a 0.2 M NaCl solution which contains 0.05% Tween 80 was used. The results are shown in Table 11. Bursting due to rupture was noted immediately after initiation of the test, and also the sustained-release property was not good. In scanning electron microscopy following the test, the occurrence of ruptures such as cracking and breaking was noted in the microcapsule coat due to the swelling of the resinate.

TABLE 11

| Time (hours) elapsed after initiation of the dissolution test | Rate (%) of methylephedrine dissolution from the microcapsules |
|---|---|
| 0 | 0 |
| 0.25 | 72.1 |
| 0.5 | 87.3 |
| 1.0 | 92.1 |
| 2.0 | 97.0 |
| 3.5 | 98.3 |
| 5.0 | 99.1 |

What is claimed is:

1. A sustained-release microcapsule preparation comprising:
   (a) an ion exchange resin which is about 6 to 16% cross-linked,
   (b) a drug adsorbed onto the ion exchange resin in an amount not less than 80% of its theoretical ion adsorption amount, and
   (c) a water-permeable polymer coating.

2. A method of producing the preparation according to claim 1, comprising adsorbing a drug in an amount not less than 80% of its theoretical ion adsorption amount onto an ion exchange resin which is about 6 to 16% cross-linked to form an ion exchange complex, and then coating the resulting ion exchange complex with a water-permeable polymer.

3. The preparation according to claim 1, wherein the ion exchange resin is a synthetic insoluble porous polymer.

4. The preparation according to claim 3, wherein the polymer is a copolymer of styrene and divinylbenzene.

5. The preparation according to claim 1, wherein the ion exchange resin is an acidic ion exchange resin.

6. The preparation according to claim 1, wherein the drug has a pKa from 6 to 10 or from 2 to 5 with a stericallybulky structure.

7. The preparation according to claim 1, wherein the drug is a drug for the respiratory tract.

8. The preparation according to claim 1, wherein the drug is a free form derived from the corresponding salt form.

9. The preparation according to claim 7, wherein the drug is dihydrocodeine, phenylpropanolamine or dl-methylephedrine.

10. The preparation according to claim 1, wherein the water-permeable polymer coating is a compound selected from the group consisting of polyacrylate, polymethacrylate, polyamide or acrylate-methacrylate copolymer.

11. The preparation according to claim 1, wherein the mean size of the microcapsule is from 5 to 1,000 μm.

12. A suspension for oral administration containing the preparation according to claim 1 in suspension in purified water.

13. The method according to claim 2, wherein the drug-ion exchange resin complex is produced by adding an ion exchange resin which is about 6 to 16% cross-linked to an aqueous solution of a drug in a free form prepared by reacting a salt of the drug with an ion exchange resin in an aqueous solvent capable of dissolving both the salt and the free form of the drug.

* * * * *